United States Patent [19]

Moses

[11] Patent Number: 5,351,926

[45] Date of Patent: Oct. 4, 1994

[54] SUPPORT STRUCTURE BEAM

[75] Inventor: James A. Moses, Dexter, Mich.

[73] Assignee: Unistrut International Corp., Ann Arbor, Mich.

[21] Appl. No.: 857,008

[22] Filed: Mar. 25, 1992

[51] Int. Cl.⁵ .................................................. A47F 5/00
[52] U.S. Cl. ................................. 248/354.5; 248/343
[58] Field of Search ..................... 248/354.5, 317, 343, 248/558; 52/729, 731.1, 732; 211/162, 113

[56] References Cited

U.S. PATENT DOCUMENTS 3,668,827  6/1972  Schwartz ......................... 52/732 X
4,564,165  1/1986  Grant et al. ......................... 248/343

Primary Examiner—Ramon O. Ramirez
Attorney, Agent, or Firm—Dykema Gossett

[57] ABSTRACT

A load support system includes a support beam. The support beam extends along a longitudinal axis and has two outwardly facing generally U-shaped framing channels separated by a web. The ratio of the depth of at least one framing channel to the height of said web is approximately 2. A support beam with at least one of the framing channels having this ratio has several advantages. It is stronger and provides for a larger variety of attachment devices to be inserted. Further, when used with respect to various channel support systems, additional support is provided under certain loading conditions.

9 Claims, 7 Drawing Sheets

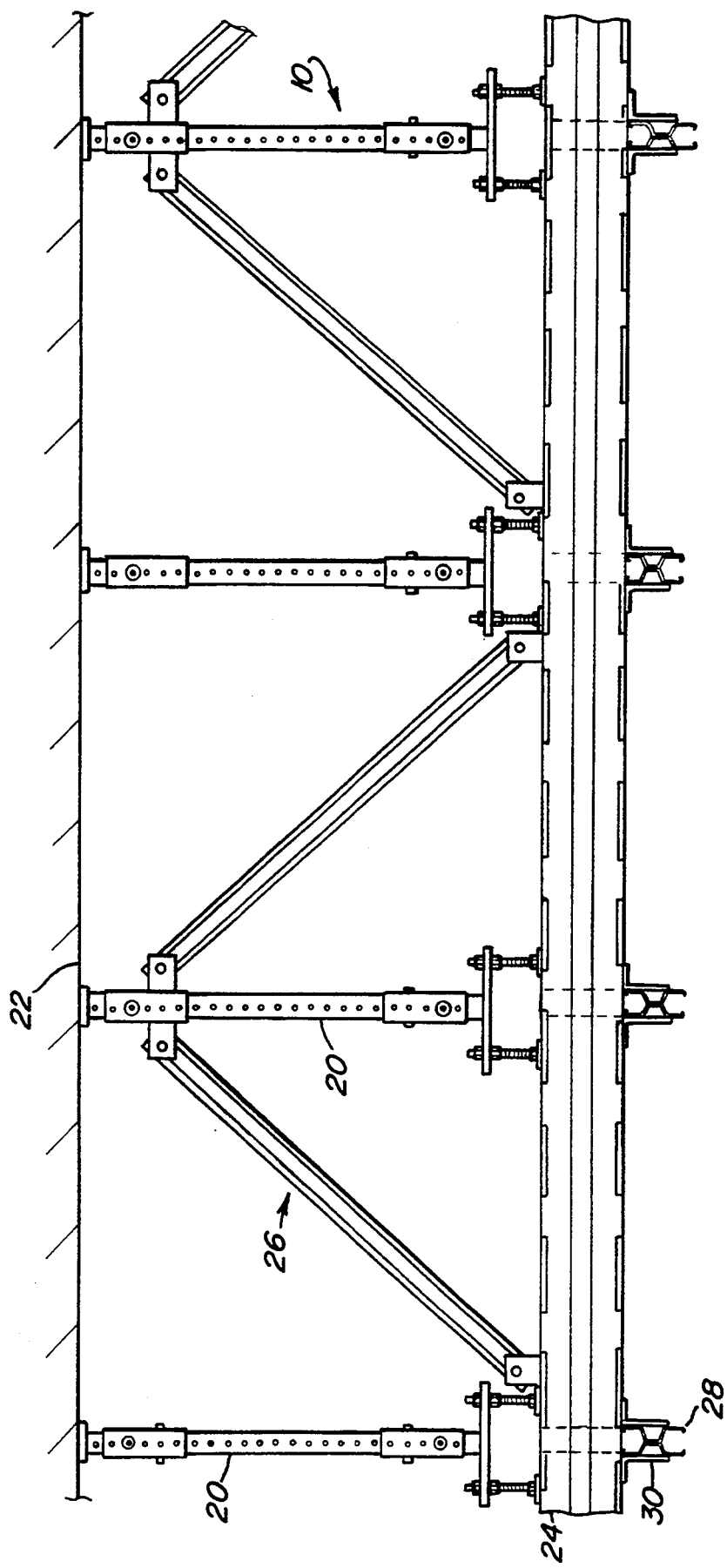

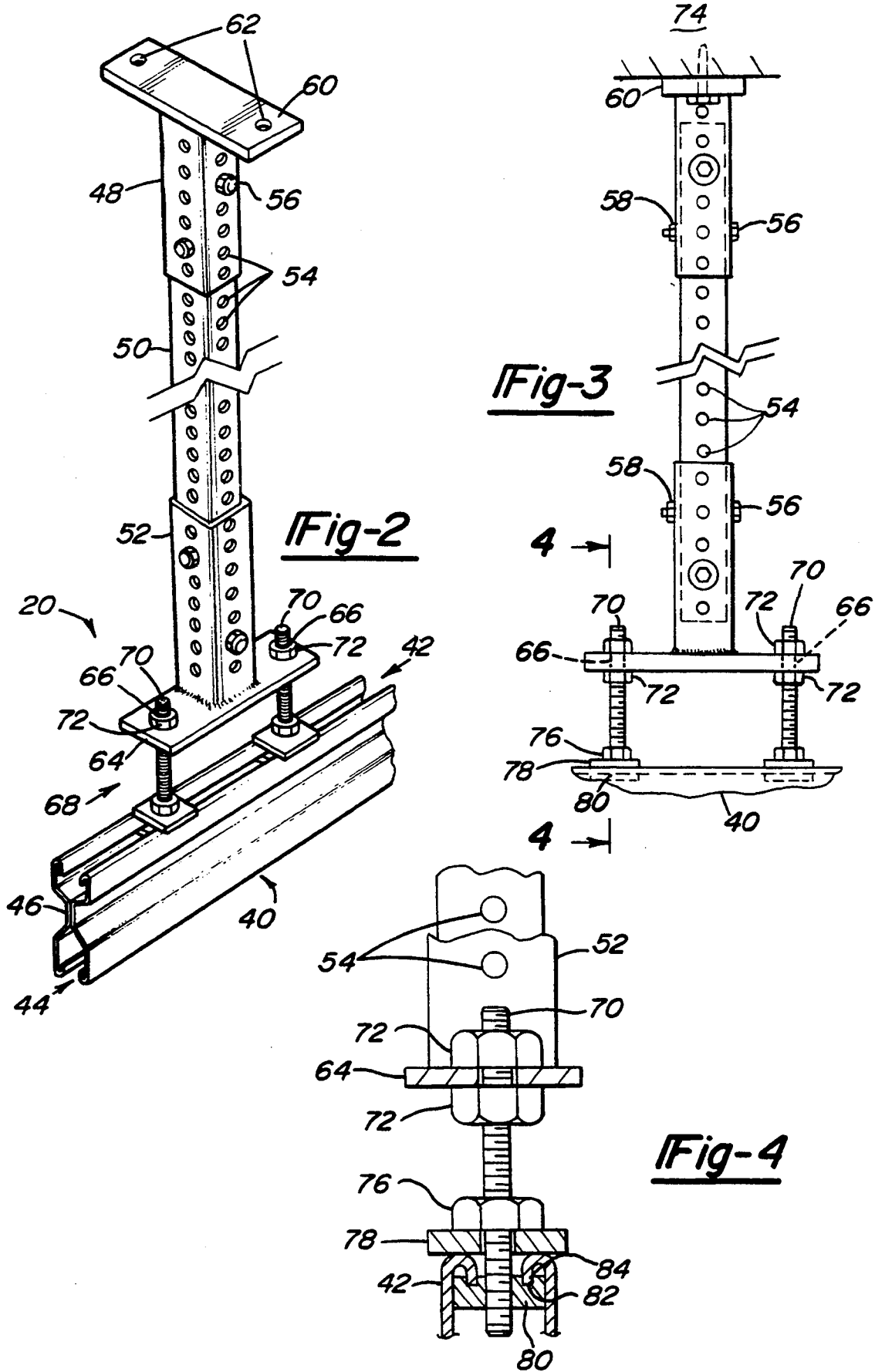

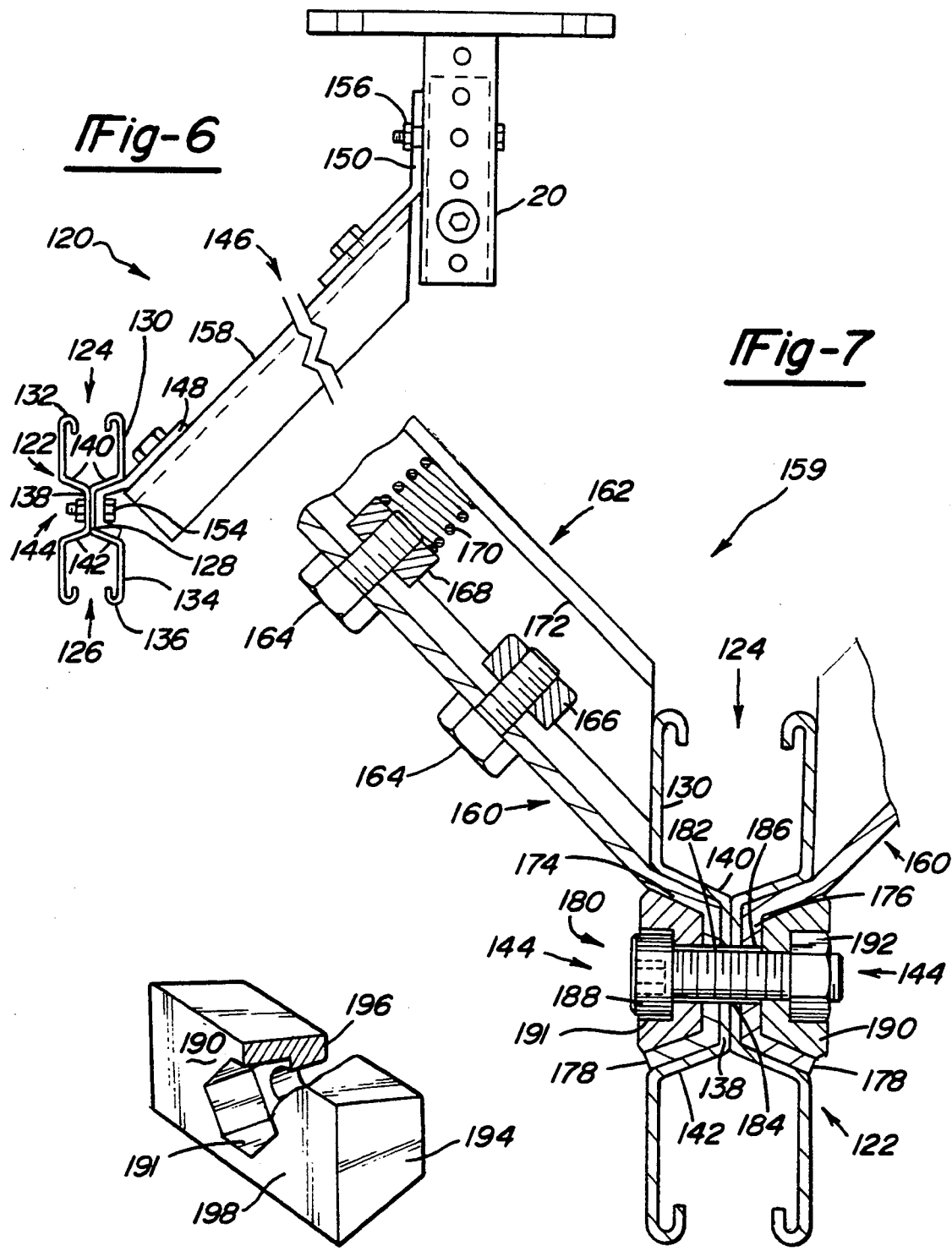

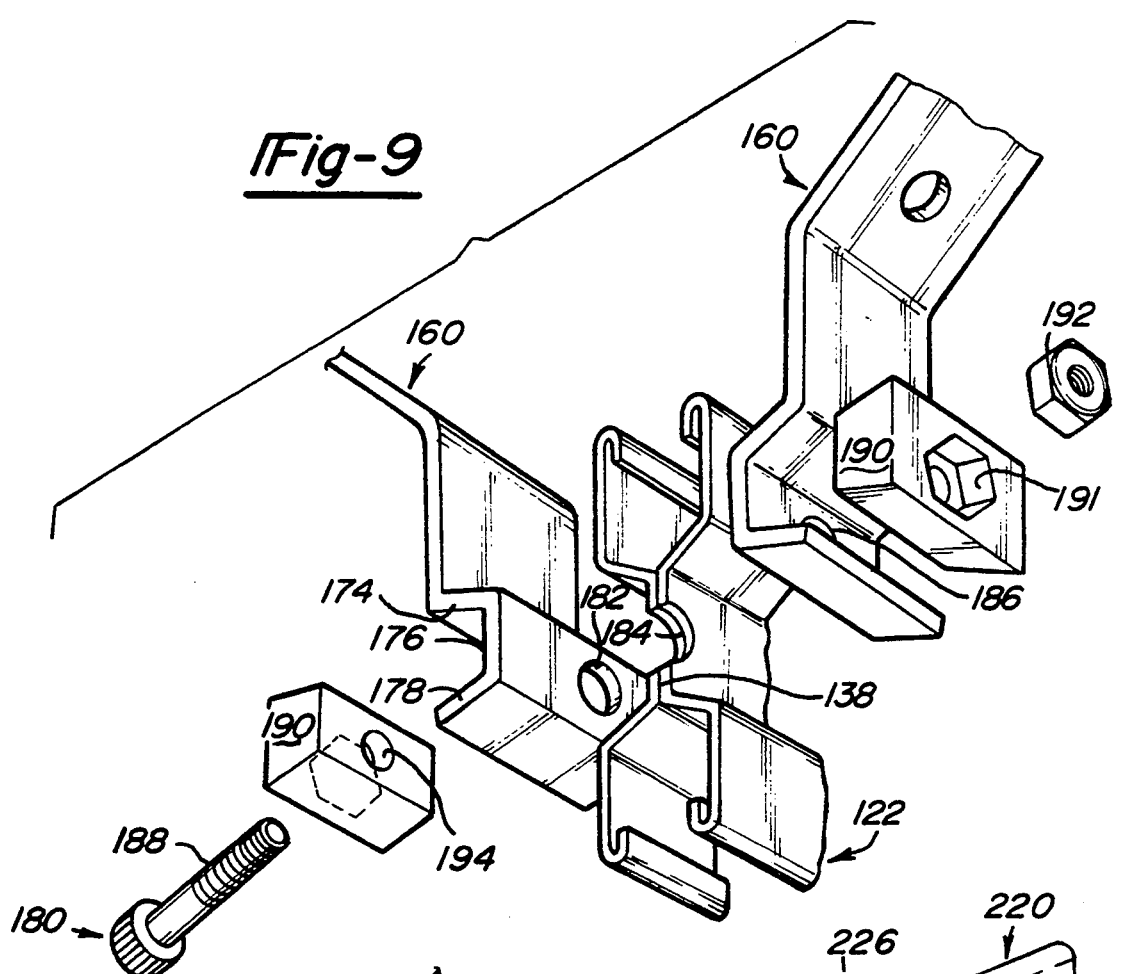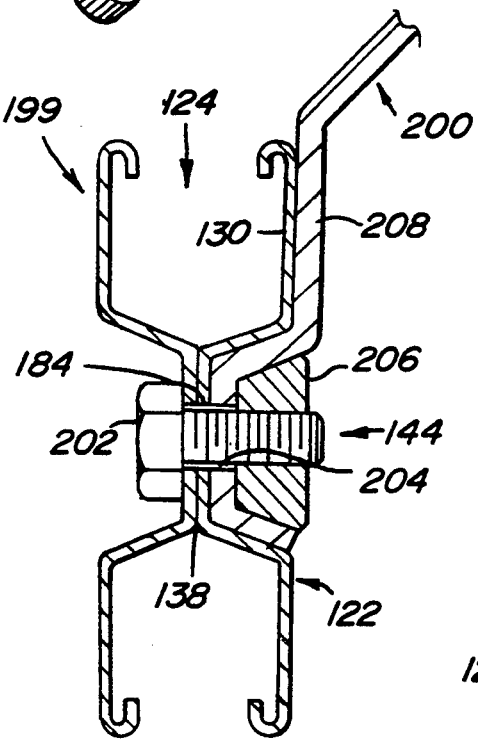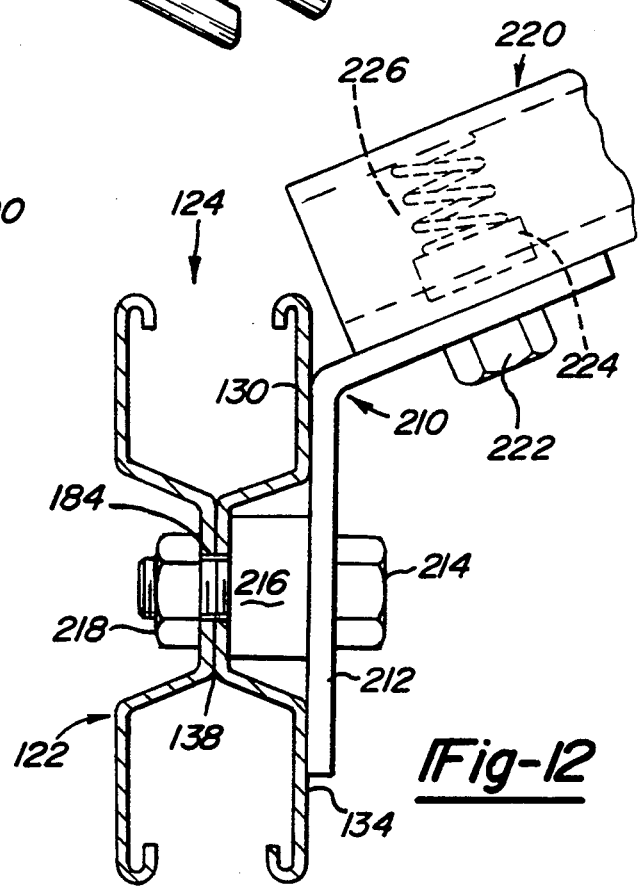

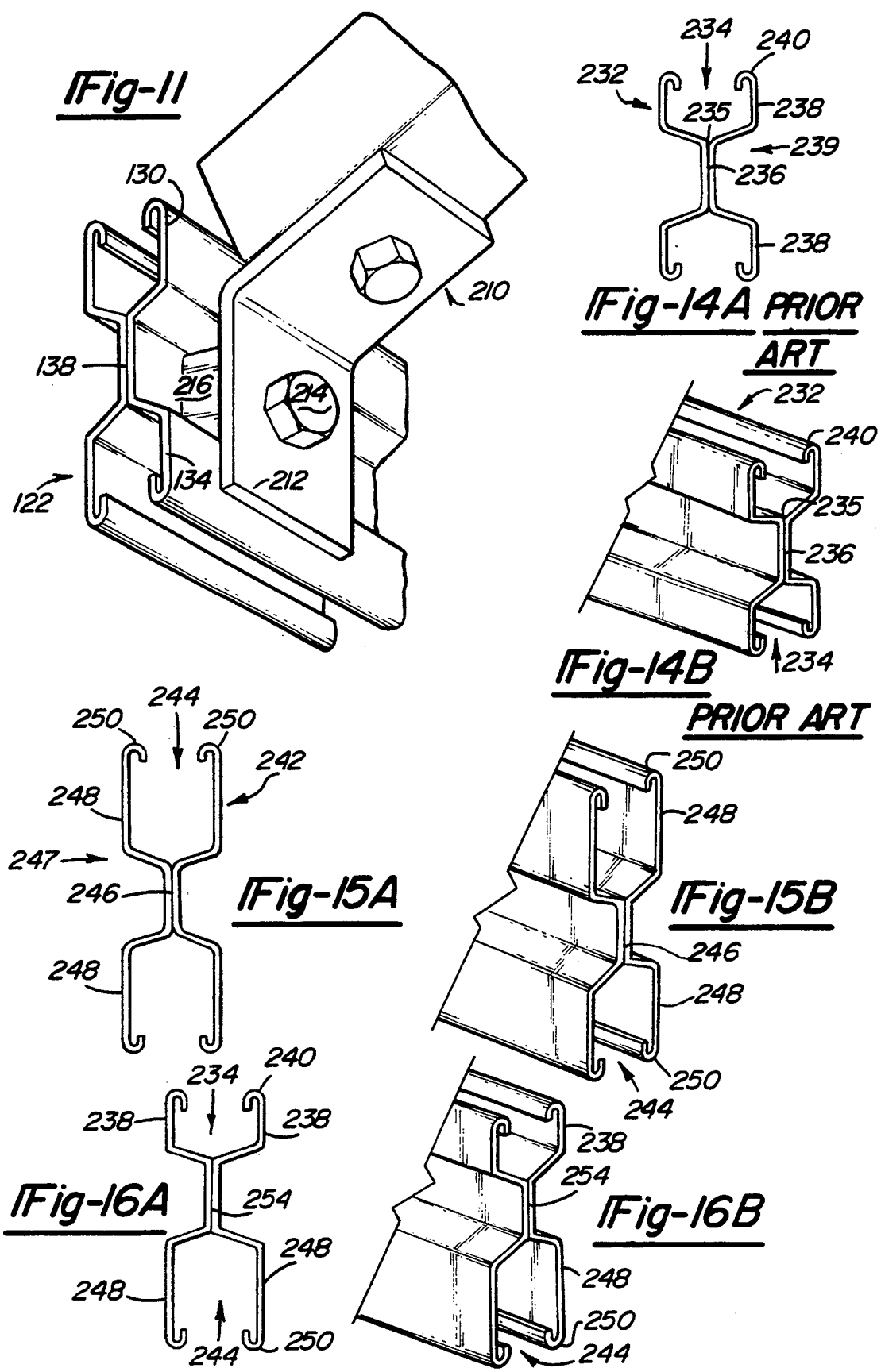

SUPPORT STRUCTURE BEAM

BACKGROUND OF THE INVENTION

This invention relates to a unique support beam for a support structure.

Prior art support structures are used to support items from a vertically upper location such as a ceiling. One common use of such support systems has been to support medical equipment such as x-ray machines.

One known support structure uses a support beam which includes two similarly sized framing channels separated by a thin web. One channel is connected by a support member to a vertically upper location while the other channel carries the supported item. The known support beams are often formed of two separate lateral members welded at the web. It would be desirable that such support beams had additional depth in the framing channels.

SUMMARY OF THE INVENTION

In a disclosed embodiment of the present invention, a support beam extends along a longitudinal axis and includes two outwardly facing generally U-shaped framing channels separated by a web. Each framing channel is defined by two flanges extending outwardly from a base, which is connected to the web.

In one embodiment of the present invention, the flanges of a first and second framing channel are longer than in the prior art. The increased depth of these framing channels allows a larger variety of attachment devices to be inserted within them. Further, when used with respect to several embodiments of channel support systems disclosed below, the increased flange length provides additional facial contact between the support beam and a diagonal bracing system. This provides additional support under certain loading conditions. In particular, when the flange is placed into compression, the load is distributed along a greater length.

In another embodiment of the present invention, the flanges of a first framing channel are shorter than the flanges of a second framing channel. Since the flanges are of different lengths, under certain load conditions the stresses from the two channels will not be focused at the center of the web. This support beam is also stronger. Additionally, the presence of at least one deeper framing channel provides for a greater variety of attachment devices to be inserted within it. Further, the presence of the longer pair of flanges help provide additional support under certain loading conditions. In particular, when the flange is placed into compression, the load is distributed along a greater length. In a preferred embodiment, the support beam is formed of two separate members welded together along the web.

These and other features of the present invention can best be understood from the following specification and drawings, of which the following is a brief description.

BRIEF DESCRIPTION OF THE DRAWINGS

FIG. 1 is a side view of a first configuration of an adjustable support system according to one embodiment of the present invention.

FIG. 2 is a perspective view of a portion of the adjustable support system.

FIG. 3 is a side view of the portion illustrated in FIG. 2.

FIG. 4 is a detail cross-sectional view along line 4—4 as illustrated in FIG. 3.

FIG. 6 is a front view of another configuration of the channel support system according to the present invention.

FIG. 7 is a cross-sectional view of another configuration of the channel support system according to the present invention.

FIG. 8 is a perspective cut away view of a washer used with the present invention shown in FIG. 7.

FIG. 9 is an exploded view of the configuration illustrated in FIG. 7.

FIG. 10 is a detailed cross-sectional view of another configuration of the channel support system according to the present invention.

FIG. 11 is a perspective view of another configuration of the channel support system according to the present invention.

FIG. 12 is an end view of the configuration illustrated in FIG. 11.

FIG. 14A is an end view of a support beam known in the prior art.

FIG. 14B is a perspective view of the prior art support beam illustrated in FIG. 14A.

FIG. 15A is an end view of a support beam according to one embodiment of the present invention.

FIG. 15B is a perspective view of the support beam illustrated in FIG. 15A.

FIG. 16A is an end view of a support beam according to another embodiment of the present invention.

FIG. 16B is a perspective view of the support beam illustrated in FIG. 16A.

DETAILED DESCRIPTION OF A DISCLOSED EMBODIMENT

Figure 5:
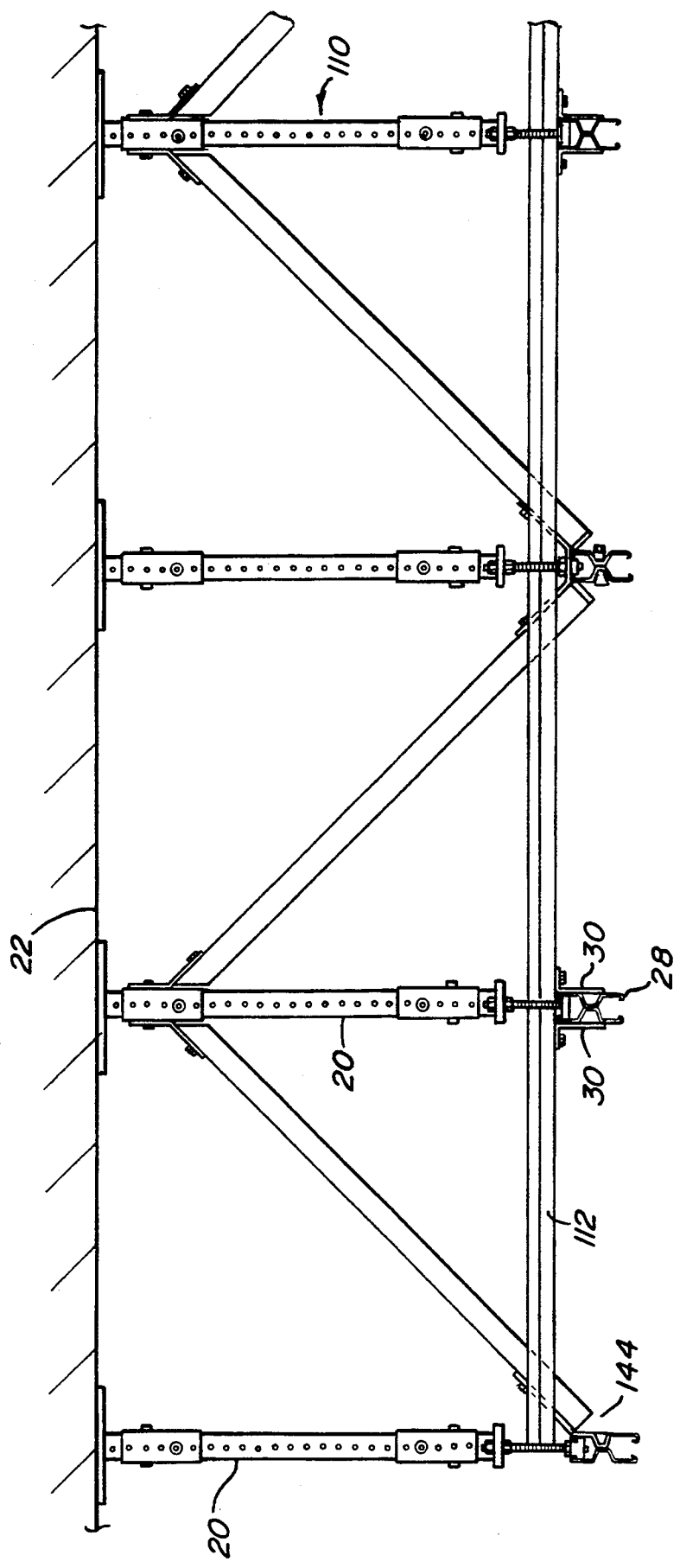
FIG. 5 is a side view of a second configuration of an adjustable support system according to the present invention.

FIG. 1 illustrates an adjustable support system 10. Telescopic columns 20 are connected at one end to a vertically upper location, such as ceiling 22 while the other end is attached to a support beam acting as a carrier rail 24. Additional support is provided through the use of lateral bracing 26 between a telescopic column 20 and the top of carrier rail 24. Support beams are used as main rails 28, which preferably support additional members. Main rails 28 may be attached to carrier rail 24 through L-brackets 30 disposed on each lateral side of a main rail 28. L-brackets 30 provide necessary support, as well as preventing undesirable twisting of a main rail 28 which may occur under certain load conditions. The attachment of a brace such as L-bracket 30 to a support beam is discussed further below.

In general, adjustable support system 10 can be reconfigured into an infinite number of configurations. In particular, the location of the various types of diagonal bracing, and additional diagonal bracings which will be disclosed below, may be rearranged with various arrangements of support beams to result in a support system individually tailored for a particular need. The various components which make up this system allow the individual systems to be specifically tailored to the particular locations and loads where items are to be supported.

FIG. 2 illustrates telescopic support column 20 attached to a support beam 40, which may be used as a carrier rail, as disclosed above. Support beam 40 has two framing channels 42 and 44 separated by a web section 46. Support column 20 may be attached either to framing channel 42 or framing channel 44. Support column 20 is formed of three four-sided column sections 48, 50, and 52. Apertures 54 extend along the sides of each of the column sections and are generally spaced equally with respect to one other. To adjust the vertical extent of support column 20, apertures 54 of one of the column sections 48, 50, and 52 are aligned with selected apertures 54 of a mating column section. A bolt 56, or similar device, is inserted through at least one set of aligned apertures 54 to achieve a selected relative position of the outer ends of the column sections. In this way, one can control the vertical position of support column 20. A nut 58, see FIG. 3, may be used to secure bolt 56 in apertures 54. Preferably, column section 50 is slidably disposed within column sections 48 and 52. The use of the three column sections 48, 50, and 52 gives increased flexibility in column length adjustment, resulting in a decreased need for expensive customized parts.

Column section 48 includes a head plate 60 welded at one end with holes 62 such that support column 20 may be attached to another structure, such as a ceiling, as shown in FIG. 1. A foot plate 64 is welded to column section 52 and has holes 66. Column section 48 and head plate 60 may preferably be identical to and interchangeable with, column section 52 and foot plate 64.

A fine height adjustment mechanism 68 threadably provides an infinite number of vertical positions for support beam 20. Screw rods 70 are slidingly inserted into holes 66 and firmly secured by tightening opposing nuts 72 against foot plate 64, as will be explained below.

As shown in FIG. 3, head plate 60 may be attached to a structure 74 to mount support beam 40. The gross outward position of head plate 60 relative to support beam 40 may be controlled by selective alignment of apertures 54 in column sections 48, 50, and 52, and using attachment devices 56, 58 as discussed above. The fine height adjustment of head plate 60 with respect to support beam 40 then consists of positioning foot plate 64 at a desired location along screw rods 70 and then tightening opposing nuts 72 against it.

Screw rods 70 are also used to detachably connect support column 20 to support beam 40. While nuts 76 and washers 78 are shown in FIG. 3, the locking mechanism is better detailed in FIG. 4. Screw rod 70 may be detachably attached to framing channel 42 with nut 76 and washer 78 outside of framing channel 42 and nut 80 within framing channel 42.

Washers 78 and nuts 80 preferably have flat peripheral wall sections to prevent rotation and may be square or hexagonal in shape. Nuts 80 should also have grooves 82 on a side wall located and sized to receive in-turned tabs 84. In this way nuts 80 are tightly captured and held in proper alignment within framing channel 42.

FIG. 5 illustrates a second configuration 110 of the basic structure illustrated in FIG. 1. As with the configuration of FIG. 1, one end of telescopic support column 20 is connected to a vertically upper location such as ceiling 22. With this configuration no carrier rail is used and the other end of telescopic support 20 is directly connected to a support beam acting as a main rail 28. To provide lateral support, lateral bracing 112 is used. Some of the main rails 28 are attached to lateral bracing 112 through the use of L-brackets 30 disposed on each lateral side of a main rail 28. As explained above with respect to FIG. 1, L-brackets 30 are used in order to prevent undesirable twisting of a main rail 28 under certain load conditions when additional support members are attached to it. Additional support and system stiffness is provided through the use of channel support system 114 between a telescopic column 20 and a main rail 28. Main rails 28 directly connected to at least one channel support system 114 may not require L-brackets 30 since channel support system 114 is designed to provide necessary support under a variety of load conditions. The inventive system allows a designer the flexibility of several configurations.

FIG. 6 illustrates a configuration 120, including a support beam 122 having two framing channels 124 and 126 separated by a web 128. Framing channel 124 is generally U-shaped with flanges 130 extending from web 128, and having in-turned tabs 132 at a free end. Framing channel 126 is generally U-shaped with flanges 134 extending from web 128 to in-turned tabs 136 at a free end.

Support beam 122 is made up of two mirror image members welded at legs 138. Legs 138 together make up web 128. Legs 140 extend at an angle laterally outwardly and away from one end of legs 138 to form a base for framing channel 124. Legs 142 extend from the opposite end of legs 138 at approximately the same angle and length as legs 140 to form a base for framing channel 126.

Support beam 122 also has two U-shaped side channels 144 laterally disposed on opposing sides of web 128. Leg 138 forms the base of a side channel 144 with legs 140 and 142 defining flanks.

Channel support system 120 includes diagonal bracing system 146. One end of diagonal bracing system 146 includes a brace 148, one end of which is disposed within a side channel 144. Support is provided with the end of brace 148 coming into nearly complete facial contact with legs 138, 140, and 142 of side channel 144. The other end of diagonal bracing system 146 includes a brace 150 secured to an upper member such as a support column 20. Brace 148 may be connected to side channel 144 in a variety of ways, including the use of nut and bolt combination 154 passing through an aperture in web 128. Similarly, brace 150 may be secured to support column 20 in a variety of ways, including the use of nut and bolt combination 156. Between braces 148 and 150 is a frame member 158. Preferably, the braces are powdered metal parts and thicker than the flanges of the support beam.

A configuration 159 shown in FIG. 7 has brace 160 attached to frame member 162 through the use of bolts 164 and nuts 166 and 168. Because of its position within frame member 162, nut 168 includes a spring 170. One end of spring 170 is attached to nut 168, with the opposite end resting against wall 172 formed within frame member 162. This aids in properly positioning nut 168 with respect to bolt 164 before they are threadingly engaged.

Preferably, braces 160 extend at an angle of between 30 and 60 degrees with respect to an axis defined by web 128 of support beam 122. More preferably, the angle is approximately 45 degrees.

The securing of braces 160 to support beam 122 is also detailed in FIG. 7. As noted above, side channels 44 could be said to be generally U-shaped. One end of brace 160 includes three integral legs 174, 176, and 178 which define an approximate U-shape that corresponds to the shape of side channel 144. When disposed within side channel 144, the inner faces of legs 174, 176, and 178 abut the outer surface of legs 138, 140, and 142 which define side channel 144. Additional support is provided by the facial contact between an end 179 of frame member 162 and the outer surface of flange 130 of support beam 122.

Braces 160 are secured by a mechanical fastener 180 passing through hole 182 in the first frame member 162, aperture 184 in web 128, and hole 186 in the second frame member 162. Mechanical fastener 182 includes bolt 188, washers 190, and nut 192.

As illustrated, more than one brace may be secured to a support beam 122 through use of a common aperture 184 in support beam 122. The use of the dual brace mounting is not restricted to a particular brace embodiment.

As shown in FIG. 8, washers 190 are trapezoidal in cross-section in a plane 194 extending perpendicular to inner face 196 and outer face 198. Inner face 196 of washer 190 fits within, and is shaped to correspond to, the outer face of legs 174, 176, and 178 of frame members 162. The corresponding shapes allow nearly complete facial contact between their mutual surfaces. This reduces the possibility of channel deformation while providing additional strength to the entire support beam.

Washer 190 includes a multi-sided recess 191. As illustrated in FIG. 7, nut 192 fits snugly within recess 191 of washer 190. The diameter of the head of bolt 188 is smaller than the recess diameter so that it does not come into contact with the sides of recess 191 when properly inserted. In order to tighten mechanical fastener 180, bolt 188 includes a slot for receiving the appropriate tightening tool, such as an "Allen" wrench. The use of such a mechanical fastener increases the space outboard of side channels 144.

FIG. 9 is an exploded view of mechanical fastener 180, braces 160 and support beam 122. To secure braces 160 they are positioned as shown in FIG. 7. Bolt 188 passes through hole 194 in first washer 190, hole 182 in first brace 160, aperture 184 in web 138, hole 186 in second brace, and threadingly engages a nut 192 which is inserted into the recess 191 of second washer 190. The trapezoidal shape of washers 190 provide a wedging action as bolt 188 is tightened in nut 192.

Another configuration 199 is shown in FIG. 10. Another embodiment brace 200 is disposed in side channel 144 in the manner discussed above. Bolt 202 passes through aperture 184 of web 138 and hole 204 of frame member 200 to threadingly engage nut 206. Nut 206 is trapezoidal in shape in the same manner as washer 190. Further support is provided under certain load conditions by the facial contact between the outer surface of flange 130 of framing channel 124 and the inner face of leg 208 on brace 200. Leg 208 extends parallel to flange 130. This is advantageous when ready access to side channel 144 is required since parts do not get in the way.

Yet another brace embodiment 210 is shown in FIG. 11. Brace 210 has end 212 with an inner face brought into facial contact with the outer surfaces of both flanges 130 and 134 of support beam 122. Brace 210 is then secured to support beam 122 by means of a bolt 214 passing through brace 212, washer 216, and web 138 to threadingly engage a nut.

As shown more clearly in FIG. 12, bolt 214 engages nut 218 after passing through aperture 184 in web 138. A free end of brace 210 is attached to frame member 220 through the use of bolt 222, nut 224 and spring 226, as disclosed above.

Figure 13A:
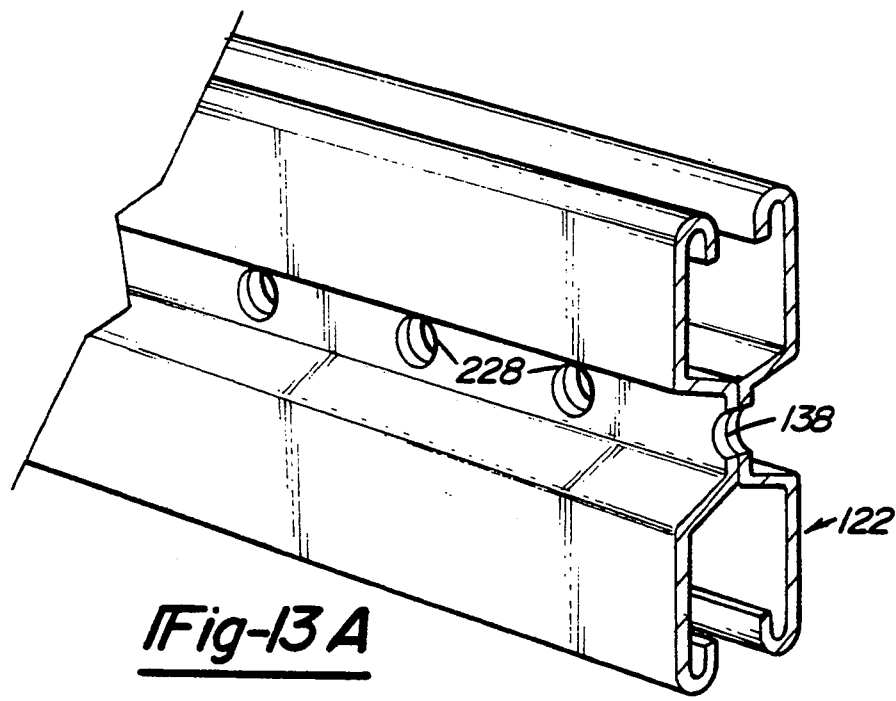
FIG. 13A is a perspective view of the support beam according to one embodiment of the present invention.
Figure 13B:
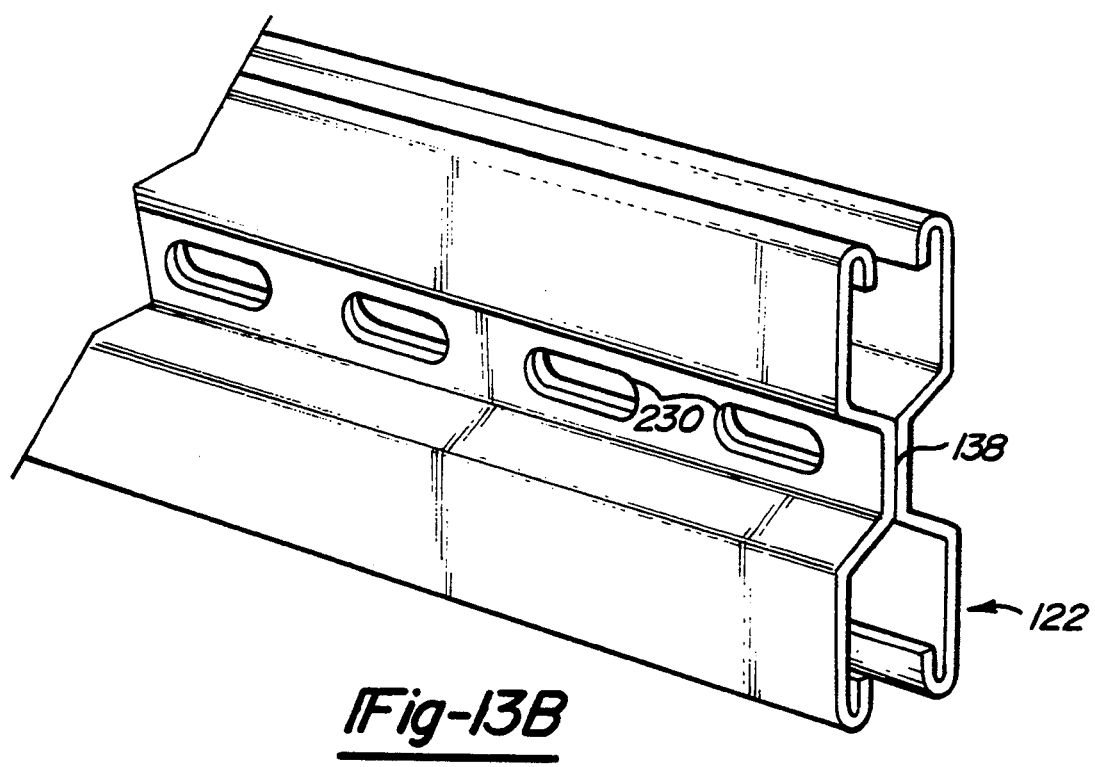
FIG. 13B is a perspective view of the support beam according to another embodiment of the present invention.

FIGS. 13A and 13B illustrate two different embodiments for connecting a support structure through web 138 of support beam 122. In each FIGURE apertures are spaced along the longitudinal extent of web 138. In FIG. 13A apertures 228 are circular and sized to receive a bolt. In FIG. 13B each aperture 230 is elongated, permitting increased adjustability along the longitudinal axis when a support structure is connected to support beam 122 through an aperture 230. While increased adjustability is an advantage, some strength may sometimes be lost through the use of elongated apertures 230 as compared to the use of smaller apertures 228 in FIG. 13A. In each case, however, the apertures are centered within web 138 along the longitudinal axis of the support beam.

The apertures within the web allow the use of a wide range of structures including the disclosed channel support systems. The mechanical fasteners within the apertures also provide increased strength to the support beam. Prior art support beams are generally both spot and arc welded. The additional strength provided by the use of mechanical fasteners passing through apertures within the web section may sometimes eliminate the need for arc welds.

FIGS. 14A and 14B illustrate a support beam 232 known in the prior art. Support beam 232 has two equally sized framing channels 234 separated by a web 236. Framing channels 234 are generally U-shaped with flanges 238 extending from web 236 to in-turned tabs 240 at a free end. The depth of the channel is defined between point 235 and an outer end of tabs 240. The ratio of the depth of each framing channel 234 to the height of web 236 is approximately 1.4. Support beam 232 also includes side channels 239. Apertures such as shown in FIGS. 13A and 13B were not included in the prior art support beam.

FIGS. 15A and 15B illustrate a support beam 242. It has two equally sized framing channels 244 separated by a web 240. In order that adjustable support systems may be used with support beam 242 and prior art support beam 232, it is preferred that side channels 247 share common dimensions with side channels 239 of support beam 232. Framing channels 244 are generally U-shaped with flanges 248 extending from web 246 to in-turned tabs 250 at a free end. Flanges 248 are longer than that found in the prior art. The ratio of the depth of each framing channel 244 to the height of web 246 is preferably approximately 2. The longer channeled support beam 242 has several advantages. The increased depth of framing channels 244 allows a larger variety of attachment devices to be inserted within them. Further, when used with respect to several embodiments of the channel support system including those disclosed in FIGS. 7, 9, and 10, the increased flange length provides additional facial contact between the support beam and the diagonal bracing system. This results in additional support under certain loading conditions. In particular, when the flange is placed into compression, the load is distributed along a greater length than is possible with respect to the prior art support beam.

FIGS. 16A and 16B illustrate a third type of support beam, 252. It has two dissimilarly sized framing channels 234 and 244, separated by a web 254. Framing channel 234 and web 236 share common dimensions with the prior art channel and web illustrated in FIGS. 14A and 14B. Framing channel 234 has flanges 238 extending from web 254 to in-turned tabs 240 at a free end. Preferably, framing channel 244 shares common dimensions with the framing channels illustrated at FIGS. 15A and 15B and has flanges 248 extending from web 254 to in-turned tabs 250. This design prevents loads on framing channel 234 from being centered at the same location as loads from framing channel 244 under certain load conditions. Additionally, the presence of at least one larger framing channel 244 provides for a larger variety of attachment devices to be inserted within it. Finally, the increased length of flanges 248 help provide additional support as was discussed with respect to support beam 242, above. The approximate ratio of the depth of framing channel 234 as compared to framing channel 244 is preferably 0.66.

Several preferred embodiments of the present invention have been disclosed. A worker of ordinary skill in the art would realize, however, that certain modifications would come within the teachings of this invention. Thus, the following claims should be studied in order to determine the true scope and content of the invention.

I claim:

1. A support beam comprising:
a body extending along a longitudinal axis, said body having two outwardly facing channels, each of said channels being formed of two laterally-spaced flanges extending outwardly from a web, wherein the ratio of the depth of one channel to the height of said web is approximately 2, and the ratio of the depth of the other of said channels to the height of said web is approximately 1.4.

2. A support beam comprising:
a body extending along a longitudinal axis, said body having two outwardly facing channels, each of said channels being formed of two laterally-spaced flanges extending outwardly from a web, said flanges of a first channel extending for a first length with said flanges of a second channel extending for a second length which is less than said first length.

3. A support beam as recited in claim 2, wherein said body is formed from two separate members which define two lateral halves of said body, and which are joined at said web.

4. A support beam as recited in claim 3, with said separate members being mirror images and each separate member has a first leg extending for a first dimension, said first leg being integrally connected to a first in-turned tab at a first end, a second leg extending laterally inwardly for a second dimension from the other of said ends of said first leg, a third leg extending for a third dimension from said second leg, a fourth leg extending laterally outwardly for a fourth dimension from said third leg, a fifth leg extending for a fifth dimension from said fourth leg to an in-turned tab integrally connected to said fifth leg, said separate members being disposed in an abutting position along said third leg, said third legs forming the web separating said first and second channels, said first legs defining said flanges of said first channel with said fifth legs defining said flanges of said second channel, said second legs defining said web for said first channel and said fourth legs defining said web for said second channel.

5. A support beam as recited in claim 4, wherein said first and fifth legs generally lie in a common lateral plane and said third legs being approximately parallel to said common lateral plane.

6. A support beam as recited in claim 5, wherein said second and fourth legs extend along planes which are non-perpendicular to said common lateral plane.

7. A support beam as recited in claim 4, wherein said members are welded to each other at said abutting position along said third leg of each of said members.

8. A support beam as recited in claim 2, wherein the ratio of the depth of said second channel to the depth of said first channel is approximately 0.66, the depth of each said channel being defined by a projection extending between the point of said web of said channel located along said longitudinal axis, and the free end of said flanges of said channel.

9. A support beam as recited in claim 2, wherein the ratio of the depth of said first channel to the height of said web is approximately 2, the depth of each said channel being defined by a projection extending between the point of said web of said channel located along said longitudinal axis, and the free end of said flanges of said channel.

* * * * *